(12) United States Patent
Flagan et al.

(10) Patent No.: US 7,407,531 B2
(45) Date of Patent: Aug. 5, 2008

(54) PARTICLE SURFACE TREATMENT FOR PROMOTING CONDENSATION

(75) Inventors: Richard C. Flagan, Pasadena, CA (US); Stanley L. Kaufman, New Brighton, MN (US); Gilmore J. Sem, Lauderdale, MN (US)

(73) Assignees: TSI Incorporated, St. Paul, MN (US); California Institute of Technology, Pasadena, CA (US)

( * ) Notice: Subject to any disclaimer, the term of this patent is extended or adjusted under 35 U.S.C. 154(b) by 403 days.

(21) Appl. No.: 11/126,002

(22) Filed: May 9, 2005

(65) Prior Publication Data

US 2005/0248750 A1    Nov. 10, 2005

Related U.S. Application Data

(60) Provisional application No. 60/569,713, filed on May 10, 2004.

(51) Int. Cl.
*G01N 1/26* (2006.01)
(52) U.S. Cl. .............................. 95/154; 356/36; 96/267; 96/413; 73/28.01; 73/863
(58) Field of Classification Search .................. 356/36, 356/37; 95/149, 154, 230; 96/243, 267, 96/413, 417; 73/28.01, 28.04, 863, 863.21
See application file for complete search history.

(56) References Cited

U.S. PATENT DOCUMENTS

| | | | |
|---|---|---|---|
| 2,684,008 A | 7/1954 | Vonnegut | 88/14 |
| 4,790,650 A | 12/1988 | Keady | 356/37 |
| 5,118,959 A | 6/1992 | Caldow et al. | 250/573 |
| 5,903,338 A | 5/1999 | Mavliev et al. | 356/37 |
| 6,712,881 B2 | 3/2004 | Hering et al. | 95/228 |
| 6,864,974 B1 | 3/2005 | Wiederin et al. | 356/316 |
| 2004/0020362 A1 | 2/2004 | Hering et al. | 95/228 |

OTHER PUBLICATIONS

Liu, W. Sl Kaufman, GJ Sem, and Fr Quant. "Material Effects on Threshold Counting Efficiency of TSI Model 3785 Water-Based Condensation Particle Counter," poster 6PDT, American Association for Aerosol Research 2004 Annual Conference, Atlanta, GA Oct. 2004, USA (2 pages).

Hering, Susanne V., Mark R. Stolzenurg, Frederick R. Quant, and Derek Oberreit. "A Laminar-Flow, Water-Based Condensation Particle Counter," platform presentation 1B1, American Association for Aerosol Research 2004 Annual Conference, Atlanta, GA, Oct. 2004, USA (1 page).

(Continued)

*Primary Examiner*—Frank M. Lawrence
(74) *Attorney, Agent, or Firm*—Patterson, Thuente, Skaar & Christensen, P.A.

(57) ABSTRACT

A system is disclosed for condensation particle counting in conjunction with modifying an aerosol to enhance the formation and growth of droplets of a selected working fluid, preferably water. Before saturation with the working fluid, the aerosol is exposed to an aerosol modifying component, preferably a vapor including molecules that are adsorbed onto surfaces of the particles or other elements suspended in the aerosol. Adsorption alters the surface character of the suspended elements towards increased affinity for the vapor of the working fluid, to promote the formation and growth of working fluid droplets. The droplets are optically detected to indicate numbers and concentrations of the suspended elements.

52 Claims, 7 Drawing Sheets

OTHER PUBLICATIONS

Susanne V. Hering and Mark R. Stolzenburg, Aerosol Dynamics Inc., Frederick R. Quant and Derek Oberreit, Quant Technologies, LLC. "A Continuous, Laminar Flow, Water-Based Condensation Particle Counter," Annual Meeting of the AAR, late breaking poster, 2003, USA (14 pages).

Washenfelder, R.A.; Roehl, C.M.; McKinney, K.A.; Julian, R.R.; Wennberg, P.O., "A Compact, lightweight gas standards generator for permeation tubes," Review of Scientific Instruments, Jun. 2003, pp. 3151-4, vol. 74, USA (8 pages).

Vici Metronics, Inc. "Generating Calibration Gas Standards with Dynacal® Permeation Devices," Houston, Texas, USA (3 pages). No Date Given.

J. McKinley and R.E. Majors, "The Preparation of Calibration Standards for Volatile Organic Compounds-A Question of Traceability," Reprinted from LCGC, vol. 18, No. 10, Oct. 2000, USA (3pages).

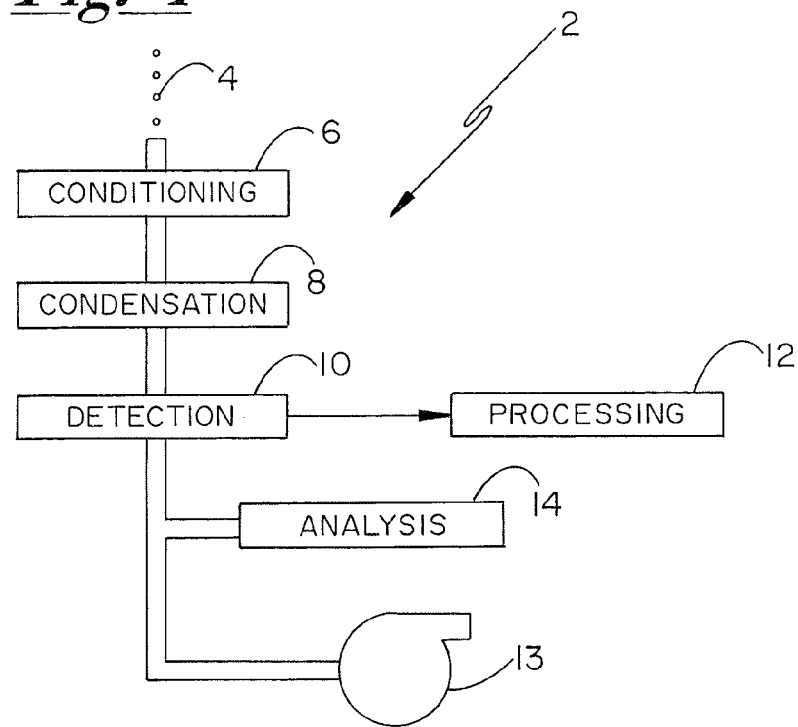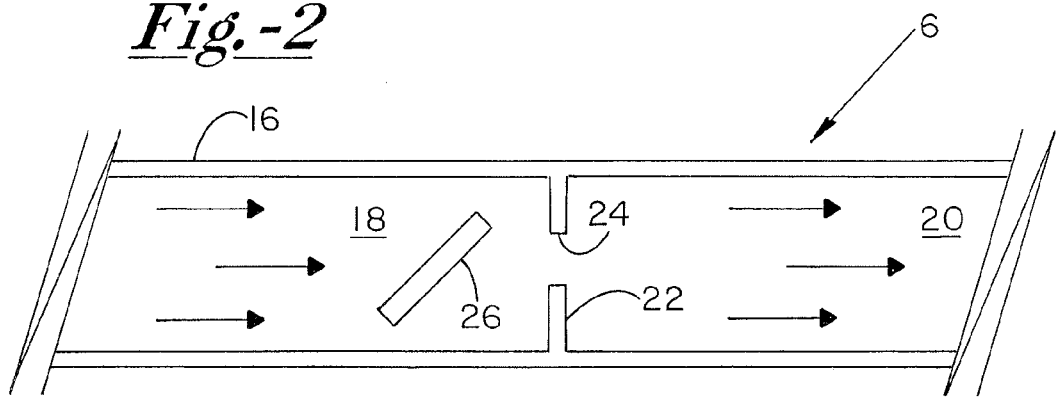

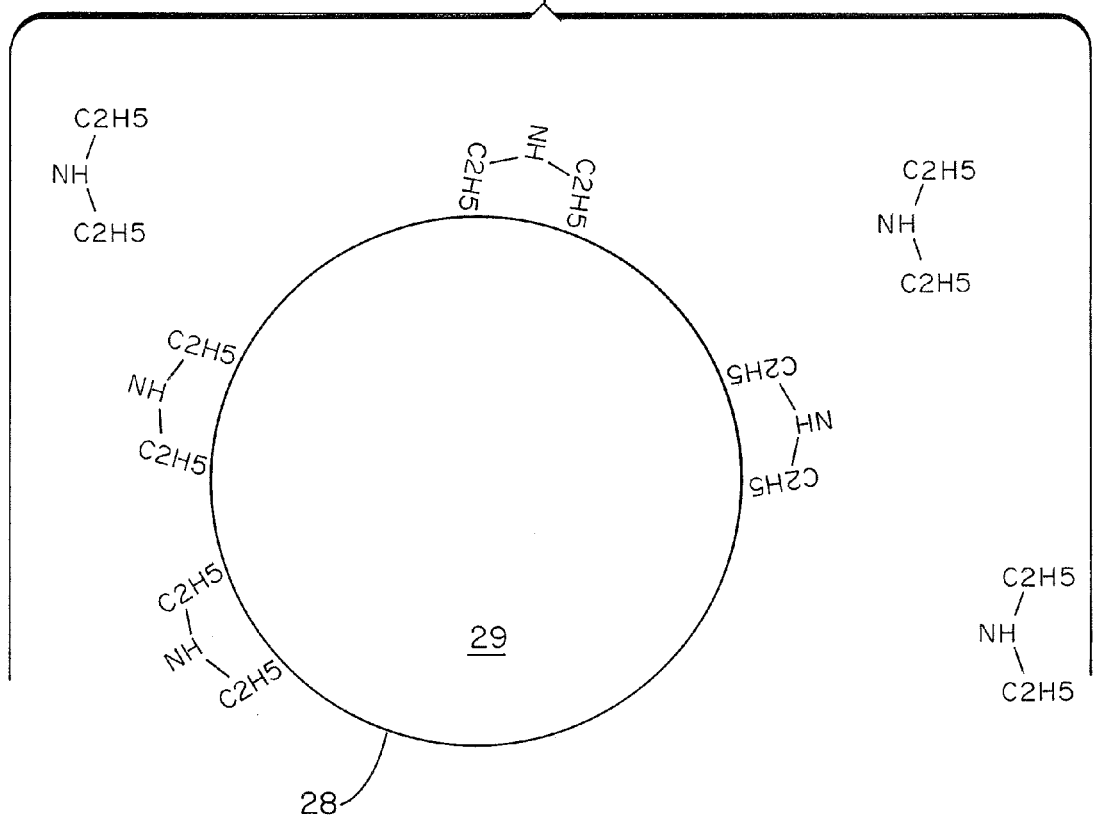

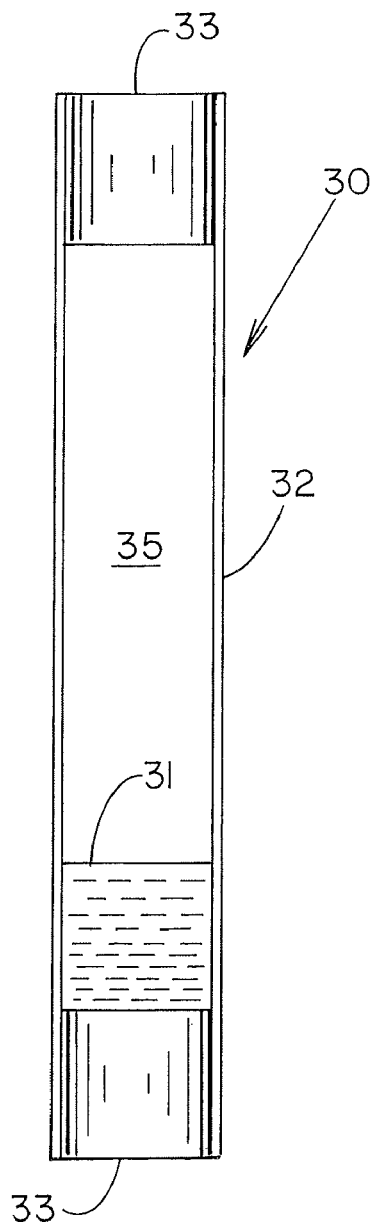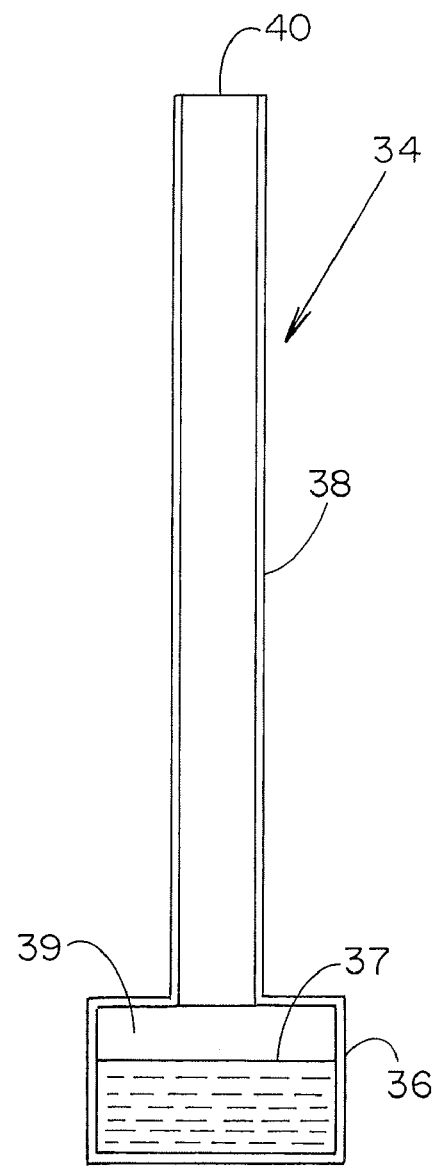

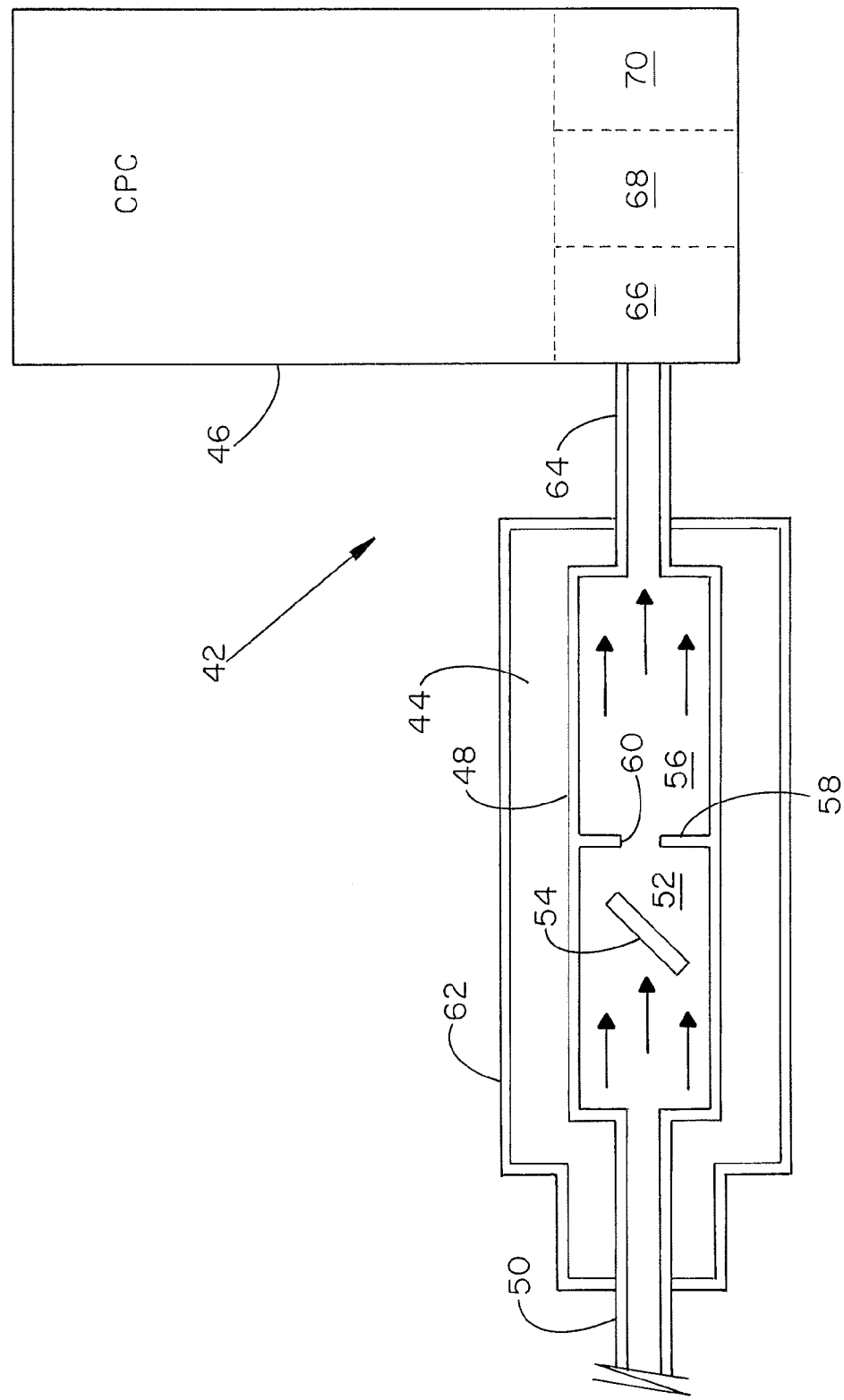

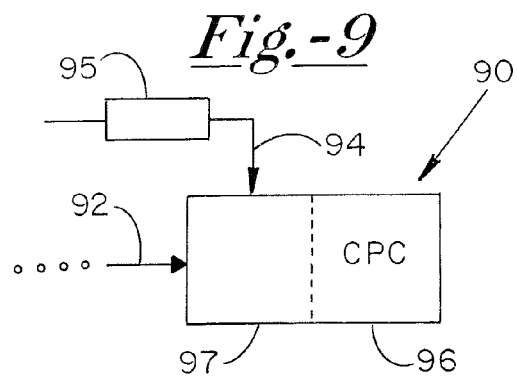
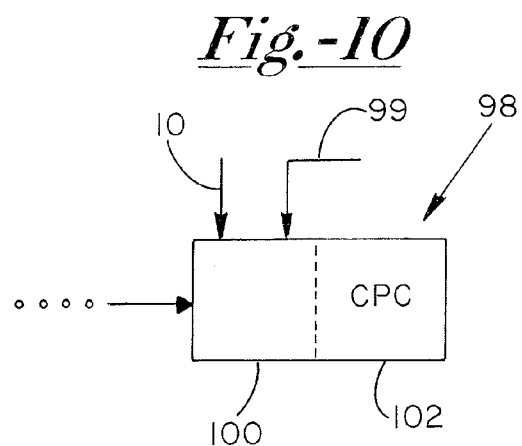
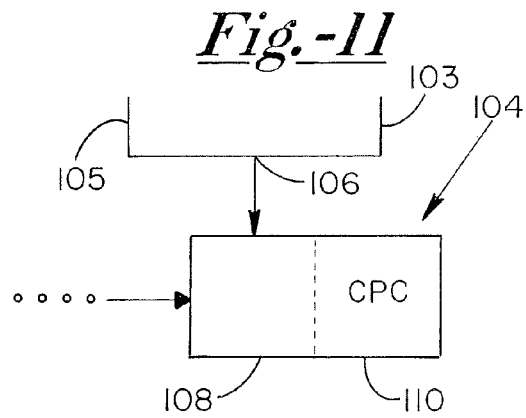
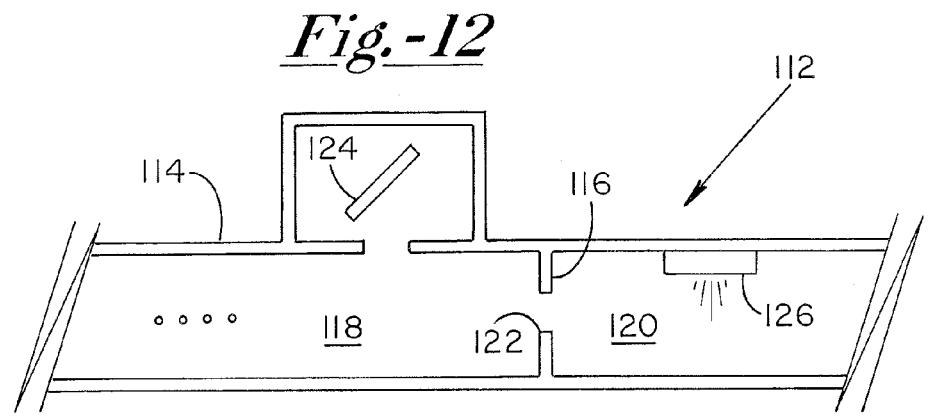

PARTICLE SURFACE TREATMENT FOR PROMOTING CONDENSATION

This application claims the benefit of priority of Provisional Application No. 60/569,713 entitled "Particle Service Treatment for Promoting Condensation," filed May 10, 2004.

BACKGROUND OF THE INVENTION

The present invention relates to the sensing of particles in the nanometer to micrometer size range, and more particularly to instruments that facilitate droplet formation and growth on particles and other elements suspended in aerosols.

A well known technique for detecting submicrometer particles (or other suspended aerosol elements, e.g. droplets) is to "grow" the elements into larger droplets through condensation of the vapor of a working fluid, thus to enhance optical detection. For example, in one form of continuous flow condensation particle counter or CPC (sometimes referred to as a condensation nucleus counter), an aerosol stream of submicrometer particles suspended in air or another gas is directed through a saturation region, where the working fluid evaporates into the aerosol stream. Upon leaving the saturation region, the aerosol stream is cooled to supersaturate the working fluid vapor. This causes the vapor to condense onto the particles, forming aerosol droplets considerably larger than the particles. The aerosol stream including the droplets is directed past an optical detection system, usually employing a laser beam and associated optics to individually sense the droplets based on scattering or interruption of the coherent energy. The droplet or particle count can be used to determine a particulate concentration in the air or other gas. Following the detection, the droplets or particles (after evaporation) may be collected for chemical analysis. For further information regarding this type of instrument, reference is made to U.S. Pat. No. 4,790,650 (Keady).

In a similar instrument known as a mixing-type CPC, an aerosol stream saturated with a working fluid vapor is mixed with a sample gas provided at a temperature lower than the aerosol temperature. This cools the gas mixture sufficiently to achieve supersaturation. As a result, particles in the gas mixture act as heterogeneous nucleation sites for condensation of the working fluid, growing droplets large enough for optical detection. Examples of this type of CPC are disclosed in U.S. Pat. No. 5,903,338 (Mavliev, et al.).

In another alternative condensation particle counter, described in U.S. Pat. No. 6,712,881 to Hering and Stolzenburg, an aerosol stream is conditioned to a desired temperature and optionally saturated, then provided to a higher-temperature condenser whose internal walls are wetted with a working fluid, preferably water. As the aerosol stream flows along the condenser, the working fluid vapor diffuses from the walls into the stream and condenses onto the particles.

Water is the preferred working fluid because of its nontoxicity, low cost, and lack of unpleasant odor. Further, water is preferred in systems that involve post-detection chemical analysis of the particles, especially in the case of biomolecules.

In conventional laminar flow condensation particle counters, working fluids with mass diffusivities lower than their thermal diffusivities are preferred, because the aerosol is cooled rather than heated as it enters the condenser. Accordingly, preferred alternative working fluids include butanol, isopropanol, and glycerol, with butanol perhaps being the most preferred. The mass diffusivity of butanol vapor, for example, is less than one-third that of water. Attempts to use water in conventional, cooled-condenser laminar flow condensation particle counters have not succeeded, although mixing-type condensation particle counters have been designed to use water as the working fluid.

In any instrument that relies on condensation to grow particles into larger droplets, the effectiveness of the technique depends on particle size and degree of supersaturation. For a given supersaturation, there is a minimum particle diameter capable of supporting growth into a droplet, commonly known as the threshold diameter. The degree of supersaturation can be controlled by controlling aerosol flow rates and temperatures along the saturation region and condenser or growth tube.

In spite of the desirable properties of water and its suitability in the Hering/Stolzenburg and mixing-type particle counter designs, its use brings to light another problem. When the working fluid is water, another variable becomes significant: the particulate material's affinity to water. Assuming that supersaturation is constant, the threshold diameter varies, from smaller threshold diameters for hydrophilic materials to larger threshold diameters for hydrophobic materials. As a result, particle counts are variable not only as a function of particle concentration, but also as a function of the character or makeup of the particles. In situations where the particle composition is unknown, or where proportions of different known particles may vary, this imposes a significant limitation on the use of water as the condensate in particle detection instruments.

Therefore, it is an object of the present invention to provide an aerosol analyzing instrument in which the formation and growth of working fluid droplets is more uniform, despite differences among suspended particles and other elements in terms of their affinity for the working fluid.

Another object is to provide a condensation particle counter capable of employing water as the working fluid, with improved sensitivity for measuring hydrophobic aerosol elements in the nanometer to micrometer diameter range.

A further object is to provide a process for modifying an aerosol to enhance droplet formation and growth on the particles and other elements suspended in the aerosol.

Yet another object is to provide a condensation particle counter capable of generating particle counts that more accurately reflect particle concentrations while minimizing the influence of extraneous factors such as particle or element makeup and affinity to the working fluid vapor.

SUMMARY OF THE INVENTION

To achieve these and other objects, there is provided a process for modifying an aerosol to enhance droplet formation and growth, including the following steps:

(a) receiving an aerosol including suspended elements capable of serving as sites for droplet formation and growth via condensation of a selected working fluid; and (b) exposing the received aerosol to an aerosol modifying component having (i) an affinity for a vapor of the selected working fluid that exceeds such affinity of at least a portion of the suspended elements, and (ii) a tendency to adhere to exposed surfaces of the suspended elements, thereby to increase a capacity in the suspended elements of said portion to form and grow droplets of the selected working fluid.

Another aspect of the invention is an apparatus for modifying an aerosol to enhance droplet formation and growth. The apparatus includes a path forming structure defining a path for accommodating an aerosol carrying suspended elements capable of serving as sites for droplet formation and growth via condensation of a selected working fluid, for movement of the aerosol along the path as an aerosol stream.

The apparatus includes a component source adapted to provide an aerosol modifying component having an affinity for a vapor of the selected working fluid that exceeds an affinity of at least a portion of the suspended elements for the working fluid vapor. The modifying component further has a tendency to adhere to exposed surfaces of the suspended elements, The component source further is adapted to introduce the aerosol modifying component into the aerosol stream at a selected location along the aerosol stream for a merger therewith. The aerosol modifying component tends to adhere to the exposed surfaces of the suspended elements, thereby increasing a capacity in the suspended elements of said portion to form and grow droplets of the selected working fluid.

A further aspect of the invention is a process for detecting elements suspended in aerosols, including the following steps:

(a) causing an aerosol, including suspended elements, to flow along a predetermined path;

(b) at a first location along the path, treating exposed surfaces of the suspended elements to increase a capacity, in at least a portion of the suspended elements, for heterogeneous nucleation of droplets of a selected working fluid onto the suspended elements;

(c) at a second location along the path, exposing the aerosol to a vapor of the selected working fluid to promote droplet formation and growth via condensation of the selected working fluid onto the suspended elements; and (d) at a third location along the path, optically detecting the droplets to generate a count indicating a number of the suspended elements.

Yet another aspect of the present invention is an apparatus for detecting elements suspended in aerosols. The apparatus includes a path forming structure defining a path for accommodating an aerosol carrying suspended elements for movement along the path. A first stage along the path is adapted to treat exposed surfaces of the suspended elements to increase a capacity in at least a portion of the suspended elements to nucleate droplets of a selected working fluid. A second stage along the path is adapted to expose the aerosol to a vapor of the selected working fluid to promote droplet formation and growth via condensation of the selected working fluid onto the suspended elements. A third stage along the path is adapted to optically detect the droplets and thereby generate a count indicating a number of the suspended elements.

In accordance with the present invention, the particles or other suspended elements in an aerosol stream are given a surface treatment prior to the droplet growth stage. This conditions particles composed of relatively hydrophobic material to increase their affinity to condensation of water vapor, preferably to a point where the treated particles are substantially equivalent to hydrophilic particles, in terms of their threshold diameters and their capacities for droplet growth.

In a preferred approach, the surface treatment involves exposure of the aerosol to a molecular vapor which is adsorbed onto the surfaces of the aerosol particles. The active components of the molecular vapor, conveniently thought of as activator molecules, are adsorbed in numbers sufficient to alter the particle character at the surface, in effect converting a hydrophobic surface to a more hydrophilic surface to reduce the particle threshold diameter toward congruence with a hydrophilic particle threshold.

The activator molecules may form a continuous layer that completely covers the surface of each particle. However, complete coverage is not required, so long as a given particle adsorbs activator molecules in numbers sufficient to substantially alter the character of the particle surface, i.e. to impart a substantially hydrophilic character. Once condensation is initiated, further condensation can take place on the water surface. It is believed that under the best conditions, surface treatment might require adsorption of only a single activator molecule on the particle surface.

In one example of this treatment, organic (e.g. hydrocarbon) particles are exposed to a vapor containing amphiphilic activator molecules. The water insoluble hydrocarbon components of the activator molecules attach to the particle surface, orienting polar water soluble components radially outwardly to attract water vapor. More particularly, diethyl amine activator molecules include hydrophobic ethane moieties that attach to the organic particle, orienting hydrophilic amine (NH) components outwardly to accept water vapor molecules.

A variety of other components may be employed to activate or condition the exposed surfaces of the elements suspended in aerosols. These include: alcohols such as ethanol and ethylene glycol; hydrocarbons including terpenes, xylenes, ethyl benzene, 1,2,4-trimethyl benzene, and toluene; organometallic compounds such as carbonyls; molecules having reactive functional groups such as carboxyl, amino, and ester groups; ammonia; acetone; and water soluble gases such as carbon dioxide and sulfur dioxide.

In addition, certain organic compounds can act as aerosol modifying components when used in conjunction with ultraviolet irradiation. Exemplary components for photoinduced activation include: o-tolualdehyde; trinitrotoluene, 2,4-dinitrotoluene, and 2,6-dinitrotoluene.

In general, aerosols can be exposed to vapors including amphiphilic activator molecules and other aerosol modifying components as noted above, to be adsorbed by the particles. This tends to equalize the affinities to water vapor among particles composed largely of hydrophobic components and particles composed largely of hydrophilic components. As a result, water can be employed as the working condensate in situations where the aerosol particles are composed of undetermined materials, or where the particles may differ considerably in their affinities to water vapor. Particles of varying compositions heterogeneously nucleate water droplets more uniformly, with minimal negative impact on particle concentration readings obtained.

The present invention is directed primarily to instruments that employ water as the condensate, because differences in affinity to water based on particle composition are more pronounced, as compared to such differences for the other commonly used working fluids. Nonetheless, this approach may be used with other working fluids, by selecting activator molecules with reference to those fluids.

IN THE DRAWINGS

For a further appreciation of the above features and other advantages, reference is made to the following detailed description and to the drawings, in which:

FIG. 1 is a block diagram of a system for analyzing aerosols, configured in accordance with the present invention;

FIG. 2 schematically illustrates an aerosol conditioning stage of the system shown in FIG. 1;

FIG. 3 schematically illustrates the adsorption of an aerosol modifying component onto the exposed surface of a hydrocarbon droplet suspended in an aerosol;

FIG. 4 shows a permeation device usable in the system of FIG. 1 to generate a vapor of the aerosol modifying component;

FIG. 5 shows a diffusion device usable in the system of FIG. 1 to generate the component vapor;

FIG. 6 illustrates a condensation particle counter incorporating a conditioning stage for modifying the aerosol in accordance with the present invention;

FIG. 9 shows part of an alternative system in which an aerosol modifying component vapor is provided directly to a saturation region of a condensation particle counter;

Figure 7:
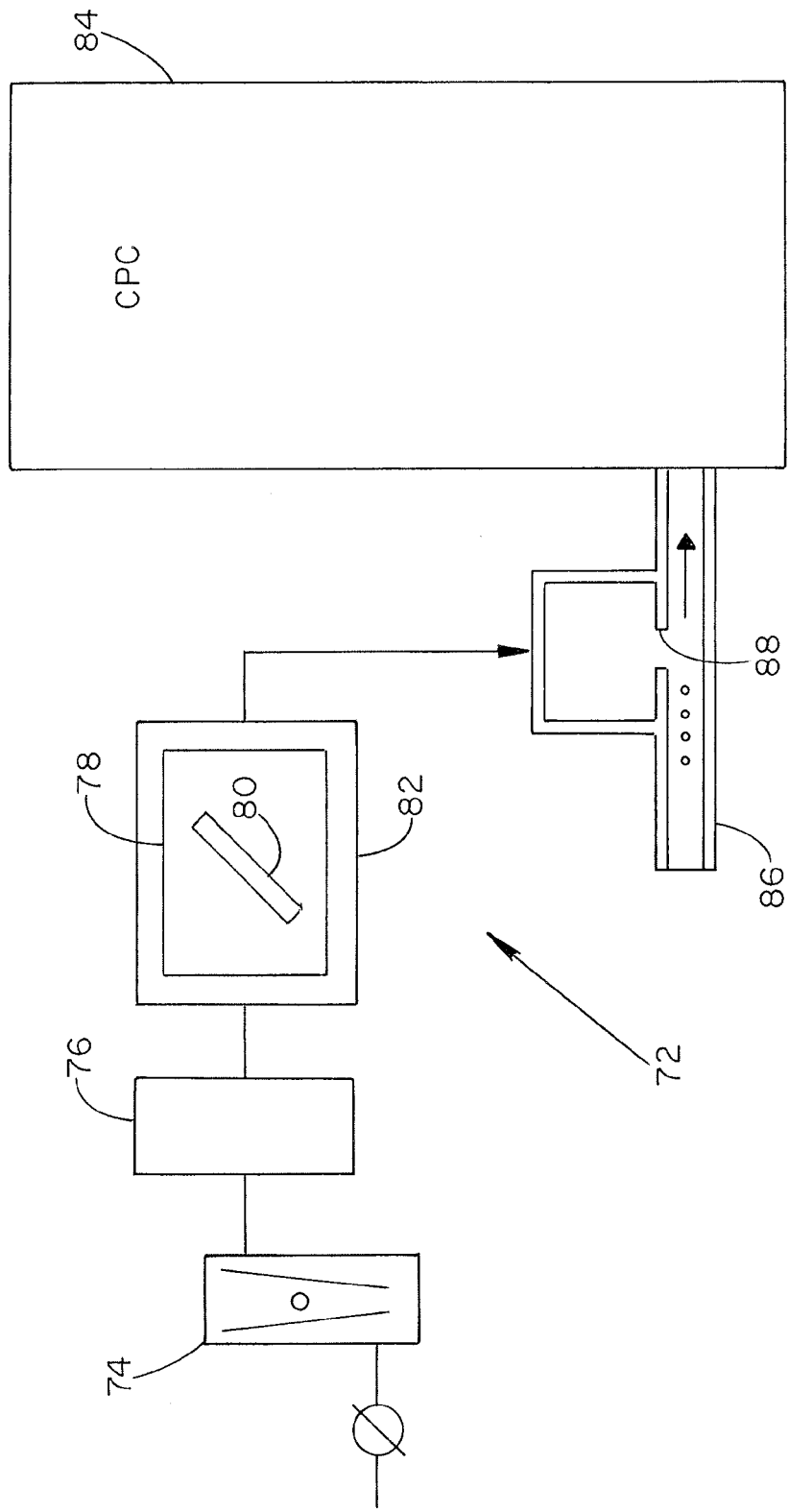
FIG. 7 illustrates an alternative embodiment system employing an auxiliary air flow to modify the aerosol.

FIGS. 10 and 11 partially illustrate alternative systems in which an aerosol modifying component and a working fluid are provided in liquid form to the saturation region of a condensation particle counter; and FIG. 12 illustrates part of an alternative embodiment system in which exposure of the aerosol to the aerosol modifying component is followed by ultraviolet irradiation.

DETAILED DESCRIPTION OF THE PREFERRED EMBODIMENTS

Turning now to the drawings, there is shown in FIG. 1 a block diagram of a system 2 for analyzing aerosols. An aerosol, including air and particles or other elements 4 suspended in the air, is provided to a conditioning stage 6, where the aerosol components are exposed to an activator vapor that consists essentially of active components suspended in a gas, typically active molecules suspended in air. The activator vapor is adsorbed onto the surfaces of the aerosol elements, altering their surfaces to promote the condensation of water vapor onto the elements. Thus, particles and other aerosol elements that initially are substantially hydrophobic, are conditioned at their surfaces and are substantially hydrophilic when carried by the aerosol to a condensation stage 8.

Along the condensation stage, the vapor of a working fluid is caused to condense onto the elements. The working fluid heterogeneously nucleates onto each particle or other element, thereby "growing" the element into a droplet much larger than the original element.

Next, the aerosol flows past an optical detection stage 10, where a laser beam and associated optical components (not shown) are used to determine a viewing volume. At least a portion of the suspended elements are carried by the aerosol stream through the viewing volume, and are detected based on scattering or interruption of the coherent energy. A particle count based on the accumulated total of scattering or interruption episodes (lower concentrations), or alternatively a current proportional to the sum of scattering by many particles (higher concentrations), is provided to a processing stage 12, and used to determine particle (or other element) concentration. A vacuum pump or other fluid moving device 13 maintains a constant aerosol flow. As an option, the droplets, or the particles after drying, are provided to a collection stage 14 for chemical analysis.

FIG. 2 illustrates conditioning stage 6 in more detail. The conditioning stage includes a conduit 16, separated into an upstream section 18 and a downstream section 20 by a wall 22. A mixing orifice 24, formed through wall 22, is sufficiently small to cause turbulent mixing in the gas flow. A vapor generator 26 disposed in upstream section 18 is used to produce an activator vapor, which becomes entrained in the aerosol gas flowing through the conduit. The activator vapor is provided to the gas at a low, uniform concentration controlled by the gas flow rate and the activator vapor release rate. The release rate is controlled primarily by maintaining vapor generator 26 at a constant temperature.

As will be appreciated from the more specific instruments discussed below, the gas entraining the activator vapor can be the aerosol itself, or a stream of filtered air or another gas destined for a merger with the aerosol. In either event, the desired concentration of activator vapor in the gas stream is provided by a steady state process in which the primary controls are the gas flow rate and the vapor generator temperature.

As mentioned above, the activator vapor carries active molecules or other components that are adsorbed onto the surfaces of the aerosol components. For example, when the working fluid is water and the aerosol components are hydrophobic, suitable active components include amphiphilic molecules. These molecules include a polar water soluble (hydrophilic) group attached to a water insoluble (hydrophobic) group such as a hydrocarbon chain.

A preferred amphiphilic activator molecule is diethyl amine. As seen in FIG. 3, each diethyl amine molecule includes a polar N—H group and two ethane moieties ($C_2H_5$). An organic aerosol element, specifically a hydrocarbon droplet 28, is shown with several diethyl amine molecules attached to its surface. Each molecule is attached by its hydrocarbon groups, orienting the amine (N—H) group radially outwardly to accept water vapor molecules. Thus, adsorption of the diethyl amine molecules in sufficient numbers changes the character of the surface 29 of hydrocarbon droplet 28, from hydrophobic to hydrophilic. While FIG. 3 shows a hydrocarbon droplet as the aerosol element, it is to be understood that adsorption of the diethyl amine molecules onto the surface of a hydrocarbon particle or other hydrophobic solid is characterized by the same orientation of the amine groups, and leads to the same result.

A surface transformation may involve complete coverage of the particle's surface with the active molecules, incomplete but considerable or substantial surface coverage, or minimal surface coverage. It is believed that under the most favorable conditions, a single adsorbed activator molecule may initiate condensation, which in turn promotes further condensation due to the presence of water on the particle or droplet surface. The degree of surface coverage necessary to promote condensation on different materials and under different conditions is not fully understood, but is presumed to vary with particle or droplet composition. The primary concern is to generate activator molecules at concentrations sufficient to achieve the degree of surface coverage necessary to activate the particles or droplets. Thus, estimates of maximum required activator vapor concentrations and diffusion times may be based on assumed values required for complete coverage. For example, the estimated surface area occupied by a diethyl amine molecule adhered to a particle surface is 0.135 $nm^2$. Based on this estimate and an assumption that the aerosol particles are spherical, a given particle size and number concentration can be used to determine the minimum number of the diethyl amine molecules required per unit volume. The time for diffusion of the active molecules to the particle surfaces may be estimated from the diffusivity of the active molecules in air (estimated from kinetic theory) and the mean distance between the active molecules (based on their number concentration). Table 1 shows results for different aerosol particle sizes and densities.

TABLE 1

| Aerosol Parameters | | Activator Molecule Concentration (Full Coverage) | | | |
|---|---|---|---|---|---|
| Diameter (nm) | Concentration (number per cm$^3$) | By Number (per cm$^3$) | By Mass (μg/m$^3$) | By Volume (ppbv)* | Diffusion Time (seconds) |
| 3 | 100 | $2.10 \times 10^4$ | $2.50 \times 10^{-6}$ | $7.80 \times 10^{-7}$ | $5.30 \times 10^{-3}$ |
| 3 | $1.00 \times 10^7$ | $2.10 \times 10^9$ | 0.25 | 0.078 | $2.50 \times 10^{-6}$ |
| 100 | 100 | $2.30 \times 10^7$ | $2.80 \times 10^{-3}$ | $8.60 \times 10^{-4}$ | $5.00 \times 10^{-5}$ |
| 100 | $1.00 \times 10^7$ | $2.30 \times 10^{12}$ | 280 | 86.4 | $2.3 \times 10^{-8}$ |

*ppbv means "parts per billion by volume."

Table 1 demonstrates that the required concentration of the diethyl amine molecules increases with the size of the aerosol particles, and also increases with the concentration of the aerosol particles. However, it also is seen that the required concentrations, in terms of micrograms per cubic meter, are well below the limits for permitted exposure, which range from 15 to 75 milligrams per cubic meter. As indicated, the calculations for Table 1 are based on full surface coverage. It is believed that the desired improvements in surface affinity for water vapor can be achieved with less than full surface coverage. With specific reference again to diethyl amine, the odor threshold is 0.13 ppm, which far exceeds the volume concentrations in Table 1.

Diethyl amine is a member of the alkyl amine group, which can be represented by the general formula:

$$N-H\begin{matrix}(CH_2)_n-CH_3\\ (CH_2)_m-CH_3\end{matrix}$$

where m and n may be zero or an integer. Table 2 includes examples of these compounds.

TABLE 2

| Name | m | n | Boiling point (degrees C.) |
|---|---|---|---|
| Dimethyl amine | 0 | 0 | 6.9 |
| Diethyl amine | 1 | 1 | 55.5 |
| Methyl ethyl amine | 0 | 1 | — |
| Propyl methyl amine | 2 | 0 | — |
| Propyl ethyl amine | 2 | 1 | — |
| Dipropyl amine | 2 | 2 | 110 |

Each of these molecules has an organic end group ($CH_3$) and an amine polar end group (N—H), and thus would be expected to improve the tendency of oil-like particles and droplets to nucleate water droplets through heterogeneous condensation of water vapor on their surfaces. The choice of molecule would be dictated by various properties including toxicity and vapor pressure. Another consideration is the boiling point, due to the desire to operate the vapor generator with the activator compound in liquid form.

Other potential activators include alcohols, e.g. ethanol. The hydroxy (OH) group is polar, while the $CH_3$ end termination groups are organic in nature. An example of an alcohol with two $CH_3$ end termination groups is 2-ethyl hexanol.

As noted above, a variety of other components may be employed to activate the exposed surfaces of the elements suspended in aerosols; for example: ethylene glycol; hydrocarbons including terpenes, xylenes, ethyl benzene, 1,2,4-trimethyl benzene, and toluene; organometallic compounds such as carbonyls; molecules having reactive functional groups such as carboxyl, amino, and ester groups; salts; ammonia; acetone; and water soluble gases such as carbon dioxide and sulfur dioxide.

In addition, certain organic compounds can act as aerosol modifying components when used in conjunction with ultraviolet irradiation. Exemplary components for photoinduced activation include: o-tolualdehyde; trinitrotoluene, 2,4-dinitrotoluene, and 2,6-dinitrotoluene.

Regardless of the active molecule employed, vapor generator 26 must be capable of steady state operation to produce low and substantially uniform concentrations of the active molecules. Two known types of devices are preferred for meeting these requirements: permeation devices and diffusion devices, both of which are used for calibrating gas chromatography equipment.

FIG. 4 shows a permeation device 30, including a tubular wall or membrane 32 and a pair of plugs 33 at opposite ends of the membrane to seal a volatile liquid 31 and its vapor 35 in a two-phase equilibrium. Membrane 32, preferably polytetrafluoroethyline (PTFE) or a fluorinated ethylene-propylene copolymer, is permeable to the vapor. Plugs 33 are impermeable.

The permeation rate, i.e. the rate at which the activator vapor is generated for entrainment into the gas flow outside the device, is controlled by several static factors, including the size (surface area) and permeability of the membrane. So long as any of the liquid remains in the device, the two-phase equilibrium is maintained, and the internal vapor pressure remains constant, in spite of a decline in the amount of liquid in the tube, and in spite of any differences in pressure outside of the tube.

The permeation rate is highly temperature sensitive. Thus, the rate of activator vapor generation can be dynamically controlled by changing the temperature, or maintained at a desired constant rate by maintaining permeation device 30 at the temperature that corresponds to the desired rate. Generally, a temperature increase of one degree Centigrade increases the permeation rate by about ten percent. The permeation device can be calibrated by weighing the device before and after steady state operation at a constant temperature for a predetermined time. To ensure permeation at the desired constant rate, it is important to stabilize the permeation device, by operating the device a sufficient time to ensure equilibration at the selected temperature. The time required for stabilization can vary, usually within a range of thirty minutes to three hours.

FIG. 5 shows an alternative active component generator in the form of a diffusion device 34. Device 34 is formed of a nonpermeable material such as glass, and includes a reservoir 36 containing a volatile liquid 37, and a vapor 39 of the volatile liquid at a substantially constant vapor pressure. Reservoir 36 is open to an elongated capillary 38. Vapor diffuses along the capillary toward an exit 40, at a substantially constant rate based on the difference between the vapor pressure in reservoir 36 and the lower vapor pressure at the exit. As it leaves capillary 38, the vapor becomes entrained in the gas flowing past the exit.

The vapor pressure inside reservoir 36 varies with the temperature at the reservoir. When the reservoir temperature is held constant, the vapor within the reservoir functions as a constant-pressure vapor source. Thus the diffusion rate in device 34, like the permeation rate in device 30, can be dynamically controlled by controlling the temperature. Typically a temperature increase of 0.2 degrees Centigrade causes about a one percent increase in the vapor flow rate through the capillary.

Other alternative generators include thermal sublimation devices which produce activator vapors from solids such as sodium chloride or other salts. In yet another approach, the activator vapor is contained in an enclosure (called a bottled vapor source) at a positive pressure, for release at a controlled rate into the aerosol stream.

FIG. 6 illustrates a system 42 including a conditioner 44 and a condensation particle counter (CPC) 46 of the Hering/Stolzenburg type disposed downstream to receive aerosol leaving the conditioner. Conditioner 44 includes a conduit 48 with an aerosol inlet 50, an upstream section 52 containing an activator vapor generator 54, a downstream section 56, and a wall 58 between the upstream and downstream sections. An orifice 60 through the wall promotes a mixing of the aerosol and the vapor, to achieve a more uniform distribution of the vapor throughout the aerosol. Conduit 48 is contained within an oven 62 that is used to maintain vapor generator 54 at a temperature corresponding to the selected vapor generation rate.

As the aerosol flows past vapor generator 54, through orifice 60 and along downstream section of conduit 56, the active molecules of the vapor are entrained into the aerosol flow and are adsorbed onto the surfaces of the aerosol particles. By the time the aerosol reaches an exit 64 of the conduit, the active molecules are attached to each particle surface in numbers sufficient to substantially cover the surfaces of the particles to alter their character from hydrophobic to hydrophilic.

Condensation particle counter 46 includes a saturation region 66, a condensation region 68, and a detection region 70. The working fluid is water. As the aerosol travels through the saturation region, water evaporates-into the stream, to a point near saturation. As the aerosol stream enters through the warmer condensation region, e.g. a growth tube, it takes up more vapor by diffusion. Because the aerosol is cooler than the saturated vapor in the growth tube, the vapor condenses onto the particles. The particles have been conditioned at their surfaces, and consequently behave as if they were composed of hydrophilic material. The threshold for droplet growth is reduced, and condensation is enhanced.

From condensation region 68, the droplets enter detection region 70 where droplets are optically detected to provide a cumulative count of detection episodes, or light scattered by multiple droplets is used to generate an electrical current indicating concentration. In the absence of particle conditioning, the detecting stage would generate different results for two sets of particles identical except for their composition, one set of particles being more hydrophilic. The primary reason is that a significant share of the more hydrophobic particles, having diameters between their threshold diameter and the lower threshold diameter for hydrophilic particles, would not heterogeneously nucleate droplets of the condensed vapor. Thus, fewer droplets would yield a lower cumulative count or lower-amplitude scattered-light signal.

In system 42, surface conditioning of the particles reduces their threshold diameter to a level at or substantially the same as the threshold diameter for hydrophilic particles, to substantially eliminate the potential for different cumulative counts or scattered-light signals based on particle composition.

FIG. 7 shows an alternative system 72 in which the aerosol particles are treated by merging the aerosol with an auxiliary air flow containing the activator vapor. The auxiliary air flow is created by directing air through a flow regulator 74 and a filter 76, after which the filtered air flows at a constant rate through a conduit 78 containing a vapor generator 80. An oven 82 is used to maintain the vapor generator at a constant temperature, corresponding to the selected rate for generating the activator vapor.

A condensation particle counter 84, which can be similar to CPC 46, receives an aerosol through an inlet conduit 86. The auxiliary air flow including the entrained active molecules, enters the inlet conduit through a mixing orifice 88, and merges with the aerosol. As the combined flows travel through conduit 86 toward CPC 84, the active molecules become adsorbed onto the surfaces of the aerosol particles.

As compared to system 42, the clean air/vapor flow in system 72 is preferentially provided at a low volume flow rate, to avoid excessively diluting the aerosol. An advantage of system 72 is that until merger, the aerosol flow is independent of the auxiliary flow. There is less of a need to thermally equilibrate the aerosol, and to adjust the aerosol flow with reference to vapor generation. Adsorption can be controlled by controlling the aerosol flow rate and the vapor generation rate. Also, oven 82 is required to heat only the auxiliary air flow, which is conveniently chosen to be a small fraction (1 to 10 percent) of the aerosol flow.

Figure 8:
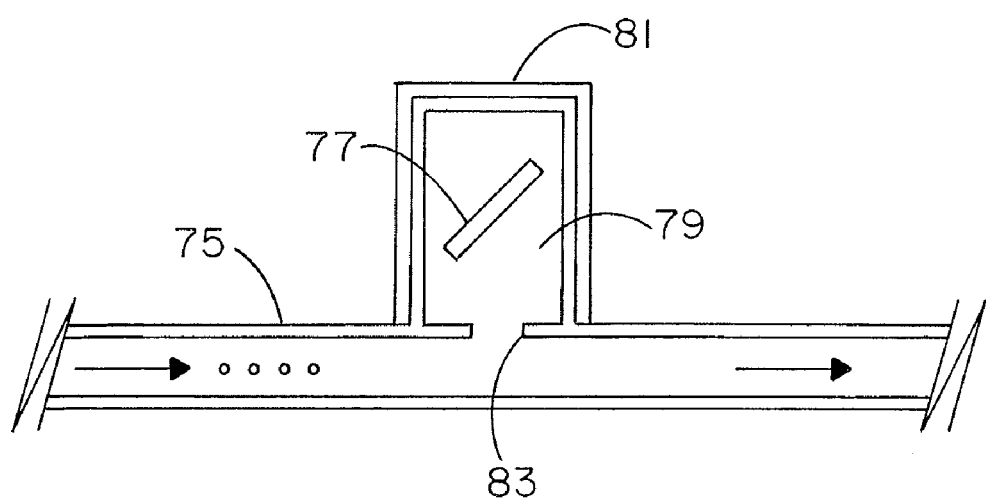
FIG. 8 illustrates an alternative aerosol modifying approach in the form of a side chamber.

FIG. 8 illustrates an alternative approach to the system in FIG. 7, in which the aerosol flows through an inlet conduit 75 toward a condensation particle counter, which is not shown in this figure. An activator vapor generator 77 is disposed in a side chamber 79, which in turn is surrounded by an oven 81 used to control the rate of vapor generation. Chamber 79 is in fluid communication with conduit 75 through an orifice 83.

The activator vapor initially accumulates in chamber 79, until reaching a state of equilibrium in which the rate of vapor generation coincides with the rate of diffusion of the vapor through orifice 83 into conduit 75.

As compared to system 72, an advantage of this approach is that no auxiliary filtered air flow is required, and thus there is no such flow to dilute the aerosol. However, to insure an even distribution of the vapor throughout the aerosol, this approach requires either structure to introduce turbulence into the aerosol flow downstream of orifice 83, or additional conduit length to provide more time for diffusion of the vapor throughout the aerosol.

FIG. 9 is a schematic view of an alternative system 90 in which an aerosol stream 92, and an auxiliary air stream 94 of filtered air entraining activator vapor at a conditioning stage 95, are provided to a condensation particle counter 96, for merger within and along a saturation region of the CPC. Concentration of the active molecules within the aerosol is controlled by controlling the aerosol flow rate and the generation rate of vapor into the filtered air flow. In system 90, the surface treatment of the aerosol particles occurs simultaneously with saturation of the aerosol stream. The saturated, conditioned aerosol stream then proceeds to the condensation and detection stages, as before.

FIG. 10 schematically illustrates another alternative system 98 in which a working fluid (water) 99 and an activating compound 101 (diethyl amine), both in liquid form, are provided simultaneously to the saturation region 100 of a condensation particle counter 102. Preferably the activating compound is injected at a point where its vapor is encountered by the aerosol upstream of the vapor of the injected working fluid, to initiate surface treatment prior to droplet growth. Conditioning is controlled by controlling the aerosol flow rate and the rate at which the activator compound is supplied to the CPC.

FIG. 11 schematically illustrates another alternative embodiment system 104 in which a working fluid and an activating compound are merged into a liquid mixture at 106, then provided to a saturation region 108 of a condensation nucleus counter 110. Surface conditioning is controlled by controlling the aerosol flow rate, and the activating fluid (liquid) supply rate.

FIG. 12 schematically illustrates an alternative conditioning stage 112 including a conduit 114. A wall 116 separates the conduit interior into an upstream section 118 and a downstream section 120. A mixing orifice 122 is formed through wall 116 to cause turbulent flow. A vapor generator 124 produces an activator vapor in the upstream section. A light source 126, disposed in downstream section 120, irradiates the aerosol and the activator vapor with energy in the ultraviolet (UV) range. The aerosol modifying component reacts to the UV energy to enhance the droplet nucleation capacities of the particles or other elements suspended in the aerosol.

Thus in accordance with the present invention, particles or other components of aerosols can be surface treated to improve their affinity to water vapor condensation, resulting in more reliable readings from condensation particle counters of the Hering/Stolzenburg design, counters of the mixing type, and other devices that depend on droplet growth through working fluid condensation. Modified aerosols increase the sensitivity of these devices, especially in terms of detecting hydrophobic particles and other elements with diameters near the low end of the nanometer-micrometer range. Surface conditioning can occur at a variety of stages, most preferably before the aerosol enters the condensation particle counter. Although the foregoing description has emphasized surface conditioning of aerosol components about to enter condensation particle counters, it is readily apparent that any aerosol analyzing instrument or system that relies on droplet growth for enhanced detection may employ this surface treatment method.

What is claimed is:

1. A process for modifying an aerosol to enhance droplet formation and growth, including:
   receiving an aerosol including suspended elements capable of serving as sites for droplet formation and growth via condensation of a selected working fluid; and
   exposing the received aerosol to an aerosol modifying component having (i) an affinity for a vapor of the selected working fluid that exceeds such affinity of at least a portion of the suspended elements, and (ii) a tendency to adhere to exposed surfaces of the suspended elements, thereby to increase a capacity in the suspended elements of said portion to form and grow droplets of the selected working fluid.

2. The process of claim 1 wherein:
   exposing the received aerosol comprises introducing a vapor of the aerosol modifying component into the aerosol.

3. The process of claim 2 wherein:
   receiving the aerosol comprises moving the aerosol along an aerosol path at a substantially constant aerosol flow rate.

4. The process of claim 3 wherein:
   exposing the received aerosol comprises introducing the component vapor at a selected location along the aerosol stream, and at a substantially constant component flow rate.

5. The process of claim 4 wherein:
   introducing the component vapor includes using a component liquid to generate the component vapor.

6. The process of claim 5 further including:
   controlling a temperature of the component liquid to generate the component vapor at the component flow rate.

7. The process of claim 5 wherein:
   generating the component vapor comprises containing the component liquid in a vapor permeable enclosure.

8. The process of claim 5 wherein:
   generating the component vapor comprises containing the component liquid in a vapor impermeable enclosure fluid coupled to an elongate capillary having a capillary exit for releasing the component vapor.

9. The process of claim 4 further including:
   exposing the received aerosol and the component vapor to ultraviolet energy at a point downstream of the selected location.

10. The process of claim 4 further including:
    causing turbulence in the aerosol stream at a point downstream of the selected location.

11. The process of claim 4 wherein:
    introducing the component vapor to the aerosol stream includes entraining the component vapor into an auxiliary gas stream then merging the auxiliary gas stream and the component vapor into the aerosol stream at the selected location.

12. The process of claim 11 further including:
    moving the auxiliary gas stream at an auxiliary stream flow rate substantially less than the aerosol flow rate.

13. The process of claim 1 wherein:
    the selected working fluid is water, and said exposing the received aerosol to an aerosol modifying component comprises selecting a component having an affinity for water vapor.

14. The process of claim 1 further including:
    after exposing the received aerosol to the aerosol modifying component, exposing the aerosol stream to the vapor of the selected working fluid.

15. The process of claim 14 wherein:
    exposing the aerosol stream to the selected working fluid vapor comprises substantially saturating the aerosol stream.

16. The process of claim 15 further including:
    after substantially saturating the aerosol stream, merging the aerosol stream with a gas maintained at a temperature lower than that of the aerosol stream to supersaturate the working fluid vapor.

17. The process of claim 14 wherein:
    exposing the aerosol stream to the vapor of the selected working fluid includes drawing the aerosol stream through a condenser having an interior wall wetted with the selected working fluid and maintained at a temperature higher than a temperature of the aerosol stream entering the condenser.

18. An apparatus for modifying an aerosol to enhance droplet formation and growth, including:
    a path forming structure defining a path for accommodating an aerosol carrying suspended elements capable of serving as sites for droplet formation and growth via condensation of a selected working fluid, for movement of the aerosol along the path as an aerosol stream; and a component source adapted to provide an aerosol modifying component having an affinity for a vapor of the selected working fluid that exceeds an affinity of at least a portion of the suspended elements for said working fluid vapor, and further having a tendency to adhere to exposed surfaces of the suspended elements;

wherein the component source further is adapted to introduce the aerosol modifying component into the aerosol stream at a selected location along the aerosol stream for a merger therewith, and wherein the aerosol modifying component tends to adhere to the exposed surfaces of the suspended elements, thereby increasing a capacity in the suspended elements of said portion to form and grow droplets of the selected working fluid.

19. The apparatus of claim 18 wherein:
the path forming structure includes a conduit for guiding the aerosol stream.

20. The apparatus of claim 18 further including:
a feature disposed along the path and downstream of the selected location, for inducing turbulence in the aerosol stream.

21. The apparatus of claim 18 further including:
a fluid conveying component for moving the aerosol along the path at a substantially constant aerosol flow rate.

22. The apparatus of claim 18 wherein:
the component source comprises a vapor source for providing the aerosol modifying component as a component vapor.

23. The apparatus of claim 22 wherein:
the vapor source is selected from a group of devices consisting of: permeation devices, diffusion devices, thermal sublimation devices, and enclosures adapted to contain the component vapor at a positive pressure.

24. The apparatus of claim 22 further including:
a heat source adapted to control a temperature of the vapor source and thereby control a rate at which the component vapor is produced.

25. The apparatus of claim 22 wherein:
the vapor source is disposed along the path.

26. The apparatus of claim 22 wherein:
the component source further includes an auxiliary gas stream adapted to entrain the component vapor, and a conduit for guiding the auxiliary gas stream from the vapor source to the selected location for the merger with the aerosol stream.

27. The apparatus of claim 26 further including:
a fluid conveying component for moving the aerosol stream at a first fluid flow rate and for moving the auxiliary gas stream at a second flow rate less than the first fluid flow rate.

28. The apparatus of claim 22 further including:
a coupling structure for fluid coupling the vapor source and the aerosol stream.

29. The apparatus of claim 28 wherein:
the coupling structure comprises an enclosure containing the vapor source.

30. The apparatus of claim 18 wherein:
the working fluid consists essentially of water, and the aerosol modifying component has an affinity for water vapor.

31. The apparatus of claim 30 wherein:
the aerosol modifying component is selected from the group of components consisting of amphiphilic compounds, alcohols, hydrocarbons, organometallic compounds, molecules having carboxyl amino and ester reactive functional groups, salts, ammonia, acetone, ethylene glycol, and water soluble gases.

32. The apparatus of claim 18 wherein:
the path forming structure comprises a wetting stage for providing the selected working fluid vapor to the aerosol stream.

33. The apparatus of claim 32 wherein:
the wetting stage is disposed downstream of the selected location, and is adapted to substantially saturate the aerosol.

34. The apparatus of claim 33 wherein:
the path forming structure comprises a condensing stage disposed downstream of the wetting stage and maintained at a temperature lower than that of the wetting stage.

35. The apparatus of claim 18 wherein:
the path forming structure comprises a condensation stage having internal walls wetted with the selected working fluid, and maintained at a condensing stage temperature higher than a temperature of the aerosol entering the condensing stage.

36. The apparatus of claim 18 further including:
an energy source disposed downstream of the selected location, for irradiating the aerosol and the aerosol modifying component with ultraviolet energy.

37. A process for detecting elements suspended in aerosols, including:
causing an aerosol, including suspended elements, to flow along a predetermined path;
at a first location along the path, treating exposed surfaces of the suspended elements to increase a capacity, in at least a portion of the suspended elements, for heterogeneous nucleation of droplets of a selected working fluid;
at a second location along the path, exposing the aerosol to a vapor of the selected working fluid to promote droplet formation and growth via condensation of the selected working fluid onto the suspended elements; and
at a third location along the path, optically detecting the droplets to generate a count indicating a number of the suspended elements.

38. The process of claim 37 wherein:
treating exposed surfaces of the suspended elements comprises applying an aerosol modifying component to the exposed surfaces, the modifying component having an affinity for the selected working fluid vapor that exceeds an affinity of said portion of the suspended elements for the selected working fluid vapor, thereby facilitating condensation of the selected working fluid onto the exposed surfaces.

39. The process of claim 38 wherein:
applying the aerosol modifying component comprises introducing a vapor of the aerosol modifying component for adsorption of the component onto the exposed surfaces.

40. The process of claim 39 wherein:
introducing the component vapor includes using a component liquid to generate the component vapor.

41. The process of claim 40 wherein:
generating the component vapor comprises containing the component liquid in a vapor permeable enclosure.

42. The process of claim 40 wherein:
generating the component vapor comprises containing the component liquid in a vapor impermeable enclosure fluid coupled to an elongate capillary having a capillary exit for releasing the component vapor.

43. The process of claim 39 wherein:

introducing the vapor of the aerosol modifying component includes entraining the component vapor into an auxiliary gas stream, then merging the auxiliary gas stream into the aerosol at the first location.

44. The process of claim 37 wherein:

exposing the aerosol to the vapor of the selected working fluid comprises substantially saturating the aerosol at the second location, then merging the aerosol with a gas having a temperature lower than that of the aerosol stream to supersaturate the working fluid vapor.

45. The process of claim 37 wherein:

exposing the aerosol stream to the vapor of the selected working fluid includes providing a condenser at the second location, wetting an interior wall of the condenser with the selected working fluid, and maintaining the interior wall at a temperature higher than a temperature of the aerosol entering the condenser.

46. An apparatus for detecting elements suspended in aerosols, including:

- a path forming structure defining a path for accommodating an aerosol carrying suspended elements for movement along the path;
- a first stage along the path adapted to treat exposed surfaces of the suspended elements to increase a capacity in at least a portion of the suspended elements to heterogeneously nucleate droplets of a selected working fluid;
- a second stage along the path adapted to expose the aerosol to a vapor of the selected working fluid to promote droplet formation and growth via condensation of the selected working fluid onto the suspended elements; and
- a third stage along the path adapted to optically detect the droplets and thereby generate a count indicating a number of the suspended elements.

47. The apparatus of claim 46 further including:

a component source adapted to provide an aerosol modifying component having an affinity for a vapor of the selected working fluid that exceeds an affinity of at least a portion of the suspended elements for said working fluid vapor, and further adapted to introduce the aerosol modifying component into the aerosol at the first stage.

48. The apparatus of claim 47 wherein:

the component source comprises a vapor source for providing the aerosol modifying component as a component vapor to be adsorbed on exposed surfaces of the suspended elements.

49. The apparatus of claim 48 wherein:

the vapor source is selected from a group of devices consisting of: permeation devices, diffusion devices, thermal sublimation devices, and enclosures adapted to contain the component vapor at a positive pressure.

50. The apparatus of claim 48 further including:

a heat source adapted to control a temperature of the vapor source and thereby control a rate at which the component vapor is produced.

51. The apparatus of claim 46 further including:

a saturation region at the second stage, substantially saturated with the working fluid vapor, and a gas source for providing a cooling gas to the second stage to supersaturate the working fluid vapor.

52. The apparatus of claim 46 further including:

a condensing means disposed at the second stage, having an interior wall wetted with the selected working fluid and maintained at a temperature higher than a temperature of the aerosol entering the second station.

\* \* \* \* \*